United States Patent
Jerger et al.

(10) Patent No.: US 6,217,588 B1
(45) Date of Patent: Apr. 17, 2001

(54) FLEXIBLE PROBE FOR USE IN LITHOTRIPSY

(75) Inventors: Thomas Jerger, Sindelfingen; Uwe Horn, Constance, both of (DE); Emanuel Goin, Lausanne (CH); Andreas Menne, Meersburg (DE)

(73) Assignee: Ferton Holding S.A., Delemont (CH)

( * ) Notice: Subject to any disclaimer, the term of this patent is extended or adjusted under 35 U.S.C. 154(b) by 0 days.

(21) Appl. No.: 09/281,364

(22) Filed: Mar. 30, 1999

(30) Foreign Application Priority Data

Mar. 31, 1998 (DE) .............................. 198 14 395

(51) Int. Cl.⁷ .................................................. A61B 17/22
(52) U.S. Cl. .......................... 606/128; 606/127; 606/170
(58) Field of Search ................... 606/170, 127, 606/128; 604/22; 128/328

(56) References Cited

U.S. PATENT DOCUMENTS

| | | |
|---|---|---|
| 3,792,701 | 2/1974 | Kloz et al. . |
| 4,605,003 * | 8/1986 | Oinuma et al. ............. 128/328 |
| 4,823,793 | 4/1989 | Angulo et al. . |
| 5,152,767 * | 10/1992 | Sypal et al. ............. 606/128 |
| 5,160,336 | 11/1992 | Favre ............. 606/128 |
| 5,387,190 | 2/1995 | Gotanda et al. . |
| 5,425,735 * | 6/1995 | Rosen et al. ............. 606/128 |
| 5,449,363 | 9/1995 | Brust et al. ............. 606/128 |
| 5,722,980 * | 3/1998 | Schulz et al. ............. 606/128 |
| 5,868,756 * | 2/1999 | Henry et al. ............. 606/128 |
| 5,906,623 * | 5/1999 | Peterson ............. 606/128 |

FOREIGN PATENT DOCUMENTS 4414903   11/1995   (DE) .

* cited by examiner

*Primary Examiner*—Gary Jackson
(74) *Attorney, Agent, or Firm*—Ratner & Prestia

(57) ABSTRACT

A metallic flexible probe for use in shock wave lithotripsy is provided next to its head portion and approximately at a transition to an adjoining initial length of the probe with a rated break point for causing without any disturbance of the energy flow along the length of the probe as optimized by different dimensional and material chracteristics of the probe a fracture at a position which most presumably will not lead to harmful injuries of the patient and to no damages of the surrounding lumen of the endoscope which is used in combination with a lithotripter.

19 Claims, 1 Drawing Sheet

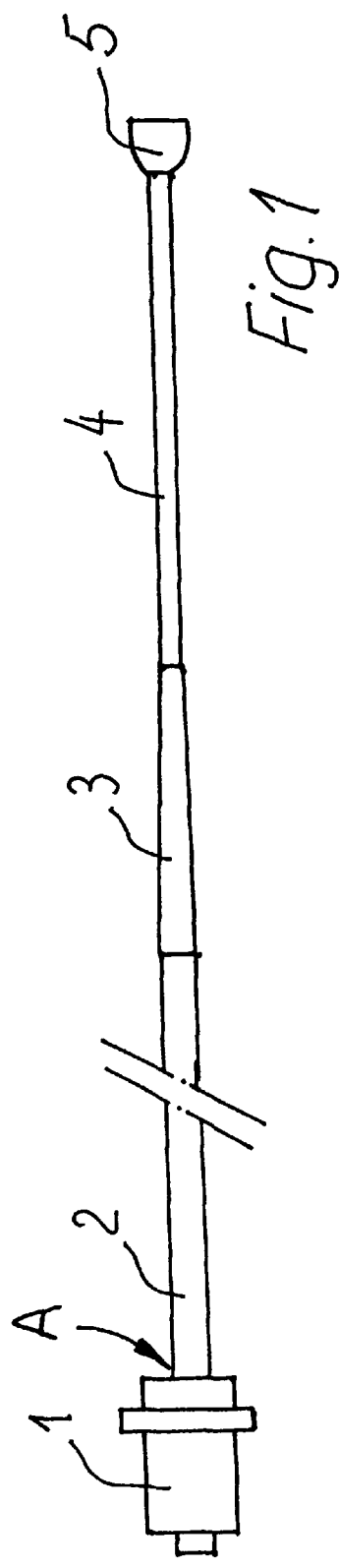
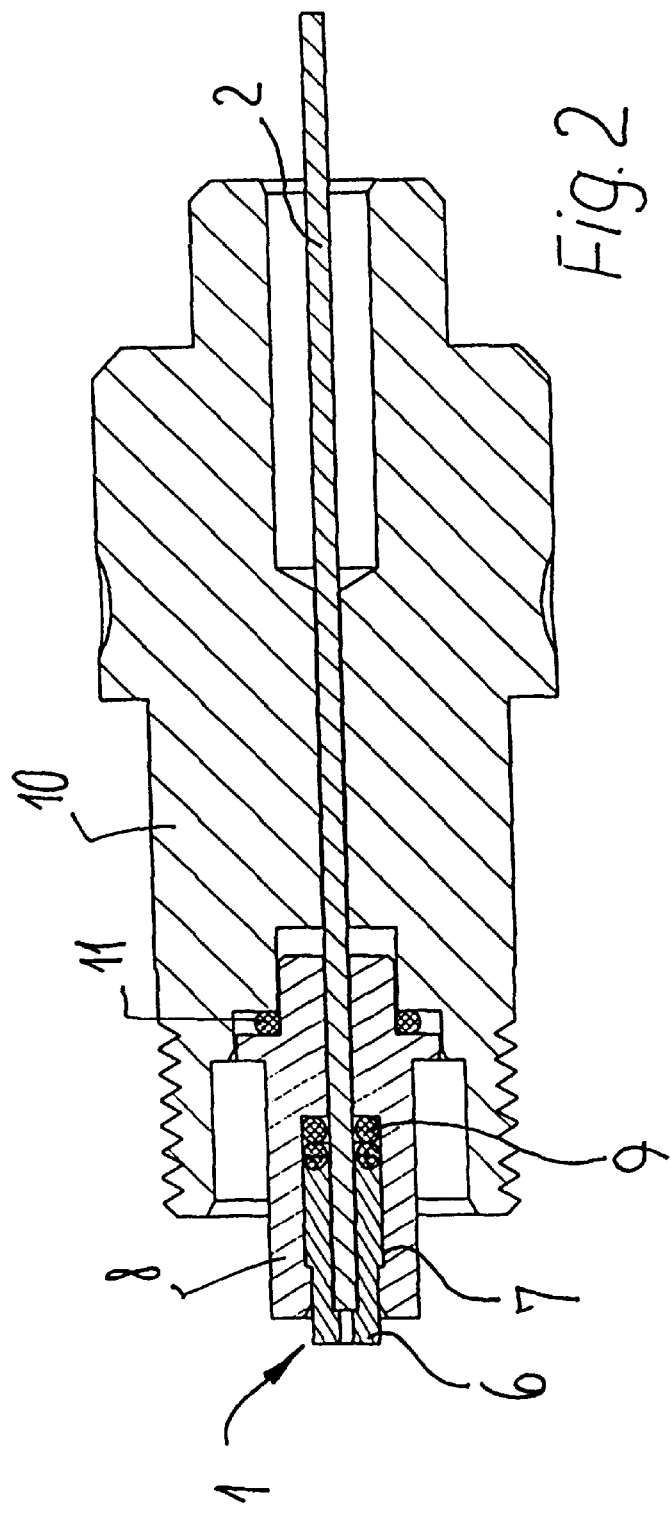
Fig. 1
Fig. 2

FLEXIBLE PROBE FOR USE IN LITHOTRIPSY

TECHNICAL FIELD

The present invention relates to a metallic flexible probe for use in lithotripsy and more particularly to a probe for use with an intracorporeal lithotripter of the kind as disclosed in U.S. Pat. No. 5,160,336 which is adapted to effect an intracorporeal fragmentation of calculi such as nephroliths, ureteroliths or urinary calculi by using an endoscope.

BACKGROUND OF THE INVENTION

U.S. Pat. No. 5,160,336 discloses an intracorporeal lithothripter having a handpiece which is adapted for holding a probe. The probe forms a waveguide which is adapted to transmit impact energy that is produced by a projectile. The projectile is pneumatically driven within a guide tube for periodically causing an impact force against the proximal end of the probe to thereby obtain shock waves at the distal end of the probe.

The efficiency of the probes as used with such lithotripters is dependent on the transfer of energy as well as also of the transformation of energy which is caused by the impact energy acting on the proximal end of the probe and being transmitted to its distal end as a shock wave resulting from such impact energy. The particular shock wave which is accordingly transmitted from a head portion to a tip portion of the probe may be considered as a repeating sequence of compressions and expansions whereby the propagation also results in a translational movement of the distal end of the probe which finally generates a deformation wave that causes the specific intracorporeal fragmentation of calculi. It is therefore to be understood that the geometric dimensions of the probe highly influence the propagation of the shock waves so that optimization of the geometric dimensions of the probe is considered as a very essential object in particular for use in a lithotripter operating with ultrasonic frequencies of the shock waves for obtaining a particle size of the calculi as fragmented by such a probe which for example may be flushed via a separate flush channel of the endoscope into which the probe has been inserted by the operator of the lithotripter.

The metallic probes which so far have been used in lithotripsy in combination with an intracorporeal lithotripter of the kind as mentioned above are usually provided with a uniform diameter of between 0.6 mm as a minimum and 3.2 mm as a maximum with an average length of the probe of about 500 mm. The probes having the smaller diameter may also be used with so-called flexible endoscopes which could also be provided with a controllable tip portion. The same mostly necessitates larger operation lengths of the probe of up to 700 mm and more for allowing a deflection of such flexible endoscopes in two directions with a circular measure by radians of up to 170°. For obtaining with such a large deflection of the endoscope a correspondingly high flexibility of the probe it already has been suggested in U.S. Pat. No. 5,449,363 to provide the probe with a flattening over the actual partial length which has to take up the deflection of the endoscope whereby the provision of such a flattening is at the same time intended to avoid any unwanted frictional contact with the surrounding wall of the lumen of the endoscope. It is further disclosed in this document that such a flattening could also allow a laser cutting or electrical discharge machining of slits at selected locations to further improve flexibility of the probe.

As the result of the relatively high stress and loading to which the head portion of the probes is exposed by the impact force as continuously produced by the pneumatically driven projectile there actually exists an enlarged risk of fractures at arbitrary portions along the length of the probe. Such fractures of the probe could lead to injuries of the patient in the course of an endoscopic treatment and could also result in damages of the wall of the working channel of the endoscope. The presence of such fractures when not timely noticed could as well tempt the operator to continue with the endoscopic treatment then even with a defective probe which would make the operation imperfect and possibly also incomplete.

SUMMARY OF THE INVENTION

The principle object of the present invention is to provide an improved probe for use more particularly in shock wave lithotripsy which will guarantee a more secure endoscopic treatment and which in general will also optimize the conditions for the transmission of the shock waves from the proximal end of the probe to its tip portion.

In accordance with the present invention a metallic flexible probe for use in lithotripsy of the kind as above referred comprises a head portion at its proximal end having a cross-section which is larger than a nominal diameter of the probe that corresponds to a predetermined lumen of an endoscope for use with an intracorporeal lithotripter, whereby a predetermined break point of the probe is provided next to its head portion and approximately at a transition to an adjoining initial length of the probe which is provided with the nominal diameter of the probe.

With the provision of such predetermined break point of the probe next to its head portion at the proximal end of the probe it should be understood that the same will have no influence on the main body of the probe extending to its tip portion at a distal end so that this main body of the probe may be designed with supplemental features in accordance with the present invention which will serve more or less the object of optimizing the transmission of the shock waves to the distal end of the probe for the purpose of an intracorporeal fragmentation of calculi as a result of the impact force and impact energy created by the pneumatically driven projectile of the lithotripter.

The predetermined break point of the probe could thusly be predetermined for example by a thermal treatment of the probe which in the vicinity of the transition to an adjoining initial length of the probe that is provided with the nominal diameter of the probe would locally weaken the strength of the probe. The predetermined break point could alternatively also be predetermined by a cross-section of the probe which in the vicinity of this specific transition is locally limited to a reduced value in comparision with the adjoining initial length of the probe and could therefore be provided for example by an indentation or a notch of the probe. Such a predetermined break point could as well be predetermined by an adhesive joint between the head portion of the probe and its adjoining initial length and as a still further alternative there could also be provided a crimp connection instead of or even supplementing such an adhesive joint.

When a predetermined break point is realised in this way then the head portion of the probe as well as its entire length may be designed in such a manner as to optimize the reception of the impact force as well as its transmission as a shock wave towards the distal end of the probe for the fragmentation of calculi. The efficiency factor of this fragmentation depends on the particular design of the probe. The initial length of the probe starting at its head portion should therefore be designed with the nominal diameter mainly under the aspect that with the propagation of the shock waves along this initial length also all existing transfer losses of the impact energy will be minimized. If most of the impact energy without any substantial transfer losses will thusly be available at the distal end of the probe this will then guarantee a most effective fragmentation of calculi without any appreciable risk of injury for the surrounding tissue so that the remaining length of the probe could then be designed with dimensional features that primarily influence the flexible behaviour of the probe without any negative influence on the propagation of the shock waves.

Under a more specific aspect of the present invention the probe is therefore preferably provided with an intermediate partial length next to its initial length having a diameter which is continuously reduced to a slightly smaller diameter at an intermediate distal end of the intermediate partial length of the probe whereby this smaller diameter remains constant over a then immediately adjoining additional partial length of the probe ending in its tip portion towards which an end portion of this additional partial length is provided with a continuous enlargement approxiamtely to the nominal diameter of the probe. The diameter of the intermediate partial length of the probe would for example be reduced along a curvature in accordance with an exponential function. The curvature could be of such a design that the intermediate distal end of the intermediate partial length of the probe is provided immediately next to the continuous enlargement which therefore would form at the same time the additional partial length of the probe in its respective entirety.

In the context of such further features of the metallic flexible probe in accordance with the present invention it of course should be understood that with the allotment of such specifically changing dimensions of the probe towards its distal end the flexibility of the probe will be optimized in such a manner as to allow the probe for being used with a flexible endoscope. Any improved flexibility as envisaged by such dimensional particularities will on the other side also have to consider the aspect that any unnecessary transitional losses of the transferred impact energy will be avoided so that finally shock waves will be presented at the distal end of the probe for the provision of a deformation wave that allows a fragmentation of the calculi to a particle size which will allow removal without any injurious influencies to the surrounding tissue.

As regards the relative length of the individual portions of the probe as well as its overall dimensional particularities it should be accepted that the same could be determined by way of experiments. It only should appear essential, however, that the initial length of the probe being provided with the nominal diameter should be made as long as possible in comparison with the remaining length of the probe so that most of the impact force acting periodically on the head portion of the probe and most of the impact energy which results from this impact force will be transferred without causing any more substantial losses of energy for the presentation of the shock waves at the distal end of the probe. The final length of the probe short of its distal end should therefore as well be dimensioned such that it still secures a sufficient concentration of shock energy for allowing an optimum fragmentation of calculi by way of an interaction with the distal end of the probe.

BRIEF DESCRIPTION OF THE DRAWINGS

Further features and advantages of the inventive flexible probe may be derived from the following description of a preferred embodiment as schematically illustrated in the drawing.

FIG. 1 is a schematic illustration of a metallic probe in accordance with the present invention.

FIG. 2 is a sectioned view of the proximal end portion of the probe and of a screw cap for fastening the probe to a handpiece of a lithotripter.

DETAILED DESCRIPTION OF THE INVENTION

As illustrated in FIG. 1 of the drawing the metallic flexible probe for use in lithotripsy comprises in accordance with the present invention a head portion 1 which has a cross-section that is larger than a nominal diameter of the probe corresponding to a predetermined lumen of an endoscope for use with an intracorporeal lithotripter.

The head portion 1 of the probe is dimensioned such that the probe may be fastened by means of a screw cap on the handpiece of a lithotripter for example of the kind as disclosed in U.S. Pat. No. 5,160,336 where by measures could be taken for allowing also to arrange a packing or sealing material which by its inherent elastic-resilient features will act as a damper for influencing the shock waves that are obtained from the impact force of a pneumatically driven projectile acting periodically against the proximal end of the probe. With different designs of such an intracorporeal lithotripter the projectile could instead also be driven by means of a hydraulic or an electromagnetic drive.

The nominal diameter of the probe that corresponds to a predeterminded lumen of an endoscope for use with an intracorporeal lithotripter is provided for an initial partial length 2 of the probe which starts immediately next to the head portion 1 of the probe. This initial partial length 2 of the probe meets the condition for transmitting a shock wave resulting from the impact force of the projectile against the head portion of the probe with a minimum loss to an intermediate length 3 of the probe. The intermediate length 3 of the probe is provided with a tapered decreasing diameter which is continuously reduced to a slightly smaller diameter at its distal end. The smaller diameter at the intermediate distal end of the intermediate partial length 3 of the probe successively remains constant over an adjoining additional partial length 4 of the probe which in combination with the intermediate partial length 3 should provide a flexibile ability of the probe that could for example allow an insertion into the lumen of a flexible endoscope adapted for being bent over a radian measure of for example up to 170°. The additional partial length 4 of the probe would therefore be dimensioned such as to fit into the lumen of a flexible endoscope which could be provided with a controllable tip portion so that flexibility of the probe would be correlated with the radian measure over which the endoscope tip could be actively bent.

The metallic flexible probe is further provided with a tip portion 5 which actually forms the distal end of the probe. This tip portion 5 immediately adjoins the additional partial length 4 of the probe and ends in a flat face which is provided with the nominal diameter of the probe. The should be noted that tip section 5 has a tapered increasing diameter which continuously enlarges from the smaller diameter of additional partial length 4 of the probe towards the nominal diameter of the face of tip portion 5. This continuous enlargement is again preferably provided with a curvature according to an exponential function, but not the same exponential function as the curvature of intermediate partial length 3 of the probe. With such a specific curvature of the continuous enlargement of the end portion the probe care is once again taken for avoiding any unnecessary loss of energy for the delivery of the shock waves at the distal end of the probe.

The metallic flexible probe as so far described consists in its entirety or only in portions thereof preferably of a nickel-titanium-alloy or of a stainless steel whereby also combinations. thereof could be used. The different portions of the probe could therefore consist of materials with different characteristic features or of materials that have been thermally treated for providing respectively different characteristic features. It thusly could be envisaged for example to provide the initial length of the probe with an increased stiffness in comparision with the remaining length of the probe whereby the different stiffness could then be obtained by means of any suitable thermal treatment of the probe. Such an increased stiffness of the initial length of the probe would then provide a higher flexibility of the remaining length of the probe which in this case would be particularly suitable for use with a flexible endoscope. As another alternative the entire probe or only portions thereof could be permanently bent with a slight curvature serving the purpose of providing a force opposite to an actuating force which is present with the handling of a flexible endoscope when being controlled on demand to receive a larger radius of movement.

In accordance with a main feature of the present invention the metallic flexible probe is further provided with a predetermined break point at a position indicated by the arrow A in FIG. 1 which is therefore next to the head portion 1 of the probe and approximately at the transition of the head portion to the adjoining initial length 2 of the probe. With the provision of such a predetermined break point care is taken of the possibility that due to a permanent and periodically exposed impact force against the proximal end of the probe by the pneumatically driven projectile of the lithotripter the fatigue of the material could turn up at any arbitrary position along the length of probe and eventually resulting in a fatigue fracture the position of which would be unknown in advance. The actual object for providing the probe with such a predetermined break point is therefore to encircle such material defaults which might only be developed during the actual use of the probe. The specific position of such a predetermined break point as indicated by the arrow A is therefore chosen under the aspect that at this particular position any fracture of the probe will most presumably not lead to harmful injuries of the patient and to no damages of the surrounding lumen of the endoscope.

Such a predetermined break point could of course be provided by a plurality of different measures. If a thermal treatment of the probe will be envisaged in general for example for the purpose of providing the initial length of the probe with an increased stiffness in comparision with the remaining length of the probe as mentioned above then such a predetermined break point could be predetermined by a thermal treatment as well in such a manner that the probe will receive a lesser strength in the vicinity of the transition between the head portion 1 and the adjoining initial length 2 of the probe.

Alternatively the predetermined break point could also be predetermined by a cross-section of the probe which in the vicinity of this transition is locally limited to a reduced value in comparison with the adjoining initial length of the probe. Such a reduced cross-section would be provided for example by an indentation or a notch of the probe.

Another possibility would be the provision of an adhesive joint between the head portion of the probe and its adjoining initial length. Also a crimp connection between the head portion 1 of the probe and its adjoining initial length 2 could be envisaged as well as a head portion of the probe having a strength which is somewhat less than the strength of the adjoining initial length of the probe and which therefore would be fractured more or less automatically after a predetermined number of hits of the pneumatically driven projectile against the proximal end of the probe.

Whereas a probe having a predetermined break point as predetermined by those different measures as mentioned above could be fastened to the handpiece of a lithotripter by means of a screw cap in the manner as disclosed in U.S. Pat. No. 5,160,336 the present invention actually prefers the more specific fastening of the probe as illustrated in FIG. 2 of the drawing. In the illustrated embodiment the probe is provided with a metallic head 6 which is attached to a proximal end of the probe with a slip-on fit or which is attached to it in any other suitable manner. The metallic head 6 is inserted into an axial bore 7 of a surrounding guide bush 8 which axially guides the proximal end of the probe with an axial extension of the bore 7.

Two flexible 0-rings 9 are received in the axial bore 7 and arranged in such a manner as to be slightly prestressed in an axial direction so as to bias the probe which at its proximal end portion is surrounded by these O-rings. The biasing force which is exerted by the two O-rings 9 on the proximal end of the probe therefore acts against the impact force on the exposed face of the metallic head 6 which is caused by the pneumatically driven projectile of the lithotripter. With such an arrangement care is as well taken for averaging the impact energy already at the head portion of the probe and subsequently over the entire length of the probe. FIG. 2 further illustrates a screw cap 10 holding the guide bush 8 in an axially displaceable manner whereby a further O-ring 11 is provided as a damper acting between the guide bush 8 and the screw cap 10. The guide bush 8 could consist of a flexible material for supplementing the biasing force in particular of the two O-rings 9 whereby especially with such a flexible material of the guide bush 8 it then would also be preferred to prepare the predetermined break point of the probe by an adhesive joint or by a crimp connection between the head portion of the probe and its adjoining initial length. In the illustrated embodiment screw cap 10 actually forms a holding means for removably holding the proximal end of the probe so that by means of this screw cap the probe may be fastenend to the handpiece of a lithotripter in a conventional manner.

We claim:

1. A metallic flexible probe for use in lithotripsy, the probe being provided as a wave guide and being dimensioned such as to be inserted into an endoscope for transmission of an impact energy between a head portion at a proximal end of the probe and a tip portion at a distal end of the probe which impact energy produces shock waves at the distal end of the probe for an intracorporeal fragmentation of calculi, wherein a) the head portion of the probe has a cross-section which is larger than a nominal diameter of the probe that corresponds to a predetermined lumen of an endoscope for use with an intracorporeal lithotripter; and b) a predetermined break point, designed to break prior to any other points on the probe, is provided next to the head portion approximately at a transition to an adjoining initial length of the probe which is provided with the nominal diameter of the probe.

2. A metallic flexible probe according to claim 1, wherein an intermediate partial length of the probe next to its initial length is provided with a diameter which is continuously reduced to a slightly smaller diameter at an intermediate distal end of the intermediate partial length of the probe, the smaller diameter remaining constant over an immediately adjoining additional partial length of the probe ending in its tip portion towards which an end portion of this additional partial length is provided with a continuous enlargement approximately to the nominal diameter of the probe.

3. A metallic flexible probe according to claim 2, wherein the diameter of the intermediate partial length of the probe is reduced along a curvature in accordance with an exponential function.

4. A metallic flexible probe according to claim 2, wherein the continuous enlargement at an end portion of the additional partial length of the probe is provided with a curvature according to an exponential function which is different from the exponential function of the curvature of the intermediate partial length of the probe.

5. A metallic flexible probe according to claim 2, wherein substantially only a distal face of the probe next to the continuous enlargement at an end portion of the additional partial length of the probe is provided with the same nominal diameter of the probe as the initial length next to the predetermined break point of the probe.

6. A metallic flexible probe according to claim 2, wherein the intermediate distal end of the intermediate partial length of the probe is provided immediately next to the continuous enlargement.

7. A metallic flexible probe according to claim 1, wherein the entire probe or portions thereof consist of a nickel-titanium-alloy, a stainless steel, or a combination thereof.

8. A metallic flexible probe according to claim 1, wherein at least a first portion of the probe has a first set of material properties that is different than a second set of material properties in a second portion of the probe, the difference between the first and second sets of material properties resulting from:

(a) the first section comprising a first material that is different than a second material comprising the second portion; or (b) the first section comprising a thermally treated section and the second portion comprising an untreated section.

9. The metallic flexible probe according to claim 8, wherein the initial length of the probe is provided with an increased stiffness in comparison with the remaining length of the probe, this different stiffness being obtained by means of a thermal treatment of the probe.

10. A metallic flexible probe according to claim 1, wherein the head portion of the probe comprises a metallic head which is inserted into an axial bore of a surrounding guide bush for the proximal end of the probe, the metallic head being slighty prestressed axially by means of a seal ring on the proximal end of the probe and inserted into the axial bore of the guide bush.

11. A metallic flexible probe according to claim 10, wherein the guide bush consists of a flexible material and forms a part of a screw cap which is adapted for mounting the probe on a handpiece of an intracorporeal lithotripter.

12. A metallic flexible probe according to claim 1, wherein the predetermined break point comprises a thermally treated section of the probe which in the vicinity of said transition locally weakens the strength of the probe.

13. A metallic flexible probe according to claim 1, wherein the predetermined break point comprises a cross-section of the probe which in the vicinity of said transition is locally limited to a reduced value in comparison with the adjoining initial length of the probe.

14. A metallic flexible probe according to claim 1, wherein the predetermined break point comprises an indentation or a notch of the probe in the vicinity of said transition.

15. A metallic flexible probe according to claim 1, wherein the predetermined break point comprises an adhesive joint between the head portion of the probe and the adjoining initial length.

16. A metallic flexible probe according to claim 1, wherein the predetermined break point comprises a crimp connection between the head portion of the probe and the adjoining initial length.

17. A metallic flexible probe according to claim 1, wherein the predetermined break point is provided by a strength of the head portion of the probe which is somewhat less than the strength of the adjoining initial length of the probe.

18. A metallic flexible lithotripsy probe having a proximal end and a distal end and adapted for insertion into an endoscope for transmission of impact energy from the proximal end to the distal end as a shock wave for causing intracorporeal fragmentation of a calculus in contact with the distal end, the probe comprising:

a head portion at the proximal end;

an initial portion adjoining the head portion;

a tip portion at the distal end; and a predetermined break point adjacent the head portion approximately at a transition between the head portion and the initial portion, the predetermined break point comprising a section of the probe that is weaker than remaining sections of the probe and that is designed to fracture prior to any of the remaining sections from repeated exposure to the impact energy.

19. The metallic flexible lithotripsy probe of claim 18 wherein the predetermined break point comprises a feature that weakens the break point relative to the remaining sections of the probe, the feature selected from the group consisting of: a thermally treated section; a reduced cross-section; an indentation; a notch; an adhesive joint; a crimp connection; and an interface between a first material strength in the head portion and a second material strength in the initial portion that is less than the first material strength.

* * * * *

UNITED STATES PATENT AND TRADEMARK OFFICE
CERTIFICATE OF CORRECTION

PATENT NO. : 6,217,588 B1 Page 1 of 5
APPLICATION NO. : 09/281364
DATED : April 17, 2001
INVENTOR(S) : Jerger et al.

It is certified that error appears in the above-identified patent and that said Letters Patent is hereby corrected as shown below:

PLEASE DELETE COLUMNS 1 LINE 1 THRU COLUMNS 8 LINE 52 AND
INSERT COLUMN 1 LINE 1 THRU COLUMN 8 LINE 53 AS ATTACHED

Signed and Sealed this

First Day of April, 2008

JON W. DUDAS
*Director of the United States Patent and Trademark Office*

FLEXIBLE PROBE FOR USE IN LITHOTRIPSY

TECHNICAL FIELD

The present invention relates to a metallic flexible probe for use in lithotripsy and more particularly to a probe for use with an intracorporeal lithotripter of the kind as disclosed in U.S. Pat. No. 5,160,336 which is adapted to effect an intracorporeal fragmentation of calculi such as nephroliths, ureteroliths or urinary calculi by using an endoscope.

BACKGROUND OF THE INVENTION

U.S. Pat. No. 5,160,336 discloses an intracorporeal lithothripter having a handpiece which is adapted for holding a probe. The probe forms a waveguide which is adapted to transmit impact energy that is produced by a projectile. The projectile is pneumatically driven within a guide tube for periodically causing an impact force against the proximal end of the probe to thereby obtain shock waves at the distal end of the probe.

The efficiency of the probes as used with such lithotripters is dependent on the transfer of energy as well as also of the transformation of energy which is caused by the impact energy acting on the proximal end of the probe and being transmitted to its distal end as a shock wave resulting from such impact energy. The particular shock wave which is accordingly transmitted from a head portion to a tip portion of the probe may be considered as a repeating sequence of compressions and expansions whereby the propagation also results in a translational movement of the distal end of the probe which finally generates a deformation wave that causes the specific intracorporeal fragmentation of calculi. It is therefore to be understood that the geometric dimensions of the probe highly influence the propagation of the shock waves so that optimization of the geometric dimensions of the probe is considered as a very essential object in particular for use in a lithotripter operating with ultrasonic frequencies of the shock waves for obtaining a particle size of the calculi as fragmented by such a probe which for example may be flushed via a separate flush channel of the endoscope into which the probe has been inserted by the operator of the lithotripter.

The metallic probes which so far have been used in lithotripsy in combination with an intracorporeal lithotripter of the kind as mentioned above are usually provided with a uniform diameter of between 0.6 mm as a minimum and 3.2 mm as a maximum with an average length of the probe of about 500 mm. The probes having the smaller diameter may also be used with so-called flexible endoscopes which could also be provided with a controllable tip portion. The same mostly necessitates larger operation lengths of the probe of up to 700 mm and more for allowing a deflection of such flexible endoscopes in two directions with a circular measure by radians of up to 170°. For obtaining with such a large deflection of the endoscope a correspondingly high flexibility of the probe it already has been suggested in U.S. Pat. No. 5,449,363 to provide the probe with a flattening over the actual partial length which has to take up the deflection of the endoscope whereby the provision of such a flattening is at the same time intended to avoid any unwanted frictional contact with the surrounding wall of the lumen of the endoscope. It is further disclosed in this document that such a flattening could also allow a laser cutting or electrical discharge machining of slits at selected locations to further improve flexibility of the probe.

As the result of the relatively high stress and loading to which the head portion of the probes is exposed by the impact force as continuously produced by the pneumatically driven projectile there actually exists an enlarged risk of fractures at arbitrary portions along the length of the probe. Such fractures of the probe could lead to injuries of the patient in the course of an endoscopic treatment and could also result in damages of the wall of the working channel of the endoscope. The presence of such fractures when not timely noticed could as well tempt the operator to continue with the endoscopic treatment then even with a defective probe which would make the operation imperfect and possibly also incomplete.

SUMMARY OF THE INVENTION

The principle object of the present invention is to provide an improved probe for use more particularly in shock wave lithotripsy which will guarantee a more secure endoscopic treatment and which in general will also optimize the conditions for the transmission of the shock waves from the proximal end of the probe to its tip portion.

In accordance with the present invention a metallic flexible probe for use in lithotripsy of the kind as above referred comprises a head portion at its proximal end having a cross-section which is larger than a nominal diameter of the probe that corresponds to a predetermined lumen of an endoscope for use with an intracorporeal lithotripter, whereby a predetermined break point of the probe is provided next to its head portion and approximately at a transition to an adjoining initial length of the probe which is provided with the nominal diameter of the probe.

With the provision of such predetermined break point of the probe next to its head portion at the proximal end of the probe it should be understood that the same will have no influence on the main body of the probe extending to its tip portion at a distal end so that this main body of the probe may be designed with supplemental features in accordance with the present invention which will serve more or less the object of optimizing the transmission of the shock waves to the distal end of the probe for the purpose of an intracorporeal fragmentation of calculi as a result of the impact force and impact energy created by the pneumatically driven projectile of the lithotripter.

The predetermined break point of the probe could thusly be predetermined for example by a thermal treatment of the probe which in the vicinity of the transition to an adjoining initial length of the probe that is provided with the nominal diameter of the probe would locally weaken the strength of the probe. The predetermined break point could alternatively also be predetermined by a cross-section of the probe which in the vicinity of this specific transition is locally limited to a reduced value in comparison with the adjoining initial length of the probe and could therefore be provided for example by an indentation or a notch of the probe. Such a predetermined break point could as well be predetermined by an adhesive joint between the head portion of the probe and its adjoining initial length and as a still further alternative there could also be provided a crimp connection instead of or even supplementing such an adhesive joint.

When a predetermined break point is realised in this way then the head portion of the probe as well as its entire length may be designed in such a manner as to optimize the reception of the impact force as well as its transmission as a shock wave towards the distal end of the probe for the fragmentation of calculi. The efficiency factor of this fragmentation depends on the particular design of the probe. The initial length of the probe starting at its head portion should therefore be designed with the nominal diameter mainly under the aspect that with the propagation of the shock waves along this initial length also all existing transfer losses of the impact energy will be minimized. If most of the impact energy without any substantial transfer losses will thusly be available at the distal end of the probe this will then guarantee a most effective fragmentation of calculi without any appreciable risk of injury for the surrounding tissue so that the remaining length of the probe could then be designed with dimensional features that primarily influence the flexible behaviour of the probe without any negative influence on the propagation of the shock waves.

Under a more specific aspect of the present invention the probe is therefore preferably provided with an intermediate partial length next to its initial length having a diameter which is continuously reduced to a slightly smaller diameter at an intermediate distal end of the intermediate partial length of the probe whereby this smaller diameter remains constant over a then immediately adjoining additional partial length of the probe ending in its tip portion towards which an end portion of this additional partial length is provided with a continuous enlargement approxiamtely to the nominal diameter of the probe. The diameter of the intermediate partial length of the probe would for example be reduced along a curvature in accordance with an exponential function. The curvature could be of such a design that the intermediate distal end of the intermediate partial length of the probe is provided immediately next to the continuous enlargement which therefore would form at the same time the additional partial length of the probe in its respective entirety.

In the context of such further features of the metallic flexible probe in accordance with the present invention it of course should be understood that with the allotment of such specifically changing dimensions of the probe towards its distal end the flexibility of the probe will be optimized in such a manner as to allow the probe for being used with a flexible endoscope. Any improved flexibility as envisaged by such dimensional particularities will on the other side also have to consider the aspect that any unnecessary transitional losses of the transferred impact energy will be avoided so that finally shock waves will be presented at the distal end of the probe for the provision of a deformation wave that allows a fragmentation of the calculi to a particle size which will allow removal without any injurious influencies to the surrounding tissue.

As regards the relative length of the individual portions of the probe as well as its overall dimensional particularities it should be accepted that the same could be determined by way of experiments. It only should appear essential, however, that the initial length of the probe being provided with the nominal diameter should be made as long as possible in comparison with the remaining length of the probe so that most of the impact force acting periodically on the head portion of the probe and most of the impact energy which results from this impact force will be transferred without causing any more substantial losses of energy for the presentation of the shock waves at the distal end of the probe. The final length of the probe short of its distal end should therefore as well be dimensioned such that it still secures a sufficient concentration of shock energy for allowing an optimum fragmentation of calculi by way of an interaction with the distal end of the probe.

BRIEF DESCRIPTION OF THE DRAWINGS

Further features and advantages of the inventive flexible probe may be derived from the following description of a preferred embodiment as schematically illustrated in the drawing.

FIG. 1 is a schematic illustration of a metallic probe in accordance with the present invention.

FIG. 2 is a sectioned view of the proximal end portion of the probe and of a screw cap for fastening the probe to a handpiece of a lithotripter.

DETAILED DESCRIPTION OF THE INVENTION

As illustrated in FIG. 1 of the drawing the metallic flexible probe for use in lithotripsy comprises in accordance with the present invention a head portion 1 which has a cross-section that is larger than a nominal diameter of the probe corresponding to a predetermined lumen of an endoscope for use with an intracorporeal lithotripter.

The head portion 1 of the probe is dimensioned such that the probe may be fastened by means of a screw cap on the handpiece of a lithotripter for example of the kind as disclosed in U.S. Pat. No. 5,160,336 whereby measures could be taken for allowing also to arrange a packing or sealing material which by its inherent elastic-resilient features will act as a damper for influencing the shock waves that are obtained from the impact force of a pneumatically driven projectile acting periodically against the proximal end of the probe. With different designs of such an intracorporeal lithotripter the projectile could instead also be driven by means of a hydraulic or an electromagnetic drive.

The nominal diameter of the probe that corresponds to a predeterminded lumen of an endoscope for use with an intracorporeal lithotripter is provided for an initial partial length 2 of the probe which starts immediately next to the head portion 1 of the probe. This initial partial length 2 of the probe meets the condition for transmitting a shock wave resulting from the impact force of the projectile against the head portion of the probe with a minimum loss to an intermediate length 3 of the probe. The intermediate length 3 of the probe is provided with a tapered decreasing diameter which is continuously reduced to a slightly smaller diameter at its distal end. The smaller diameter at the intermediate distal end of the intermediate partial length 3 of the probe successively remains constant over an adjoining additional partial length 4 of the probe which in combination with the intermediate partial length 3 should provide a flexibile ability of the probe that could for example allow an insertion into the lumen of a flexible endoscope adapted for being bent over a radian measure of for example up to 170°. The additional partial length 4 of the probe would therefore be dimensioned such as to fit into the lumen of a flexible endoscope which could be provided with a controllable tip portion so that flexibility of the probe would be correlated with the radian measure over which the endoscope tip could be actively bent.

The metallic flexible probe is further provided with a tip portion 5 which actually forms the distal end of the probe. This tip portion 5 immediately adjoins the additional partial length 4 of the probe and ends in a flat face which is provided with the nominal diameter of the probe. It should be noted that tip section 5 has a tapered increasing diameter which continuously enlarges from the smaller diameter of additional partial length 4 of the probe towards the nominal diameter of the face of tip portion 5. This continuous enlargement is again preferably provided with a curvature according to an exponential function, but not the same exponential function as the curvature of intermediate partial length 3 of the probe. With such a specific curvature of the continuous enlargement of the end portion the probe care is once again taken for avoiding any unnecessary loss of energy for the delivery of the shock waves at the distal end of the probe.

The metallic flexible probe as so far described consists in its entirety or only in portions thereof preferably of a nickel-titanium-alloy or of a stainless steel whereby also combinations thereof could be used. The different portions of the probe could therefore consist of materials with different characteristic features or of materials that have been thermally treated for providing respectively different characteristic features. It thusly could be envisaged for example to provide the initial length of the probe with an increased stiffness in comparison with the remaining length of the probe whereby the different stiffness could then be obtained by means of any suitable thermal treatment of the probe. Such an increased stiffness of the initial length of the probe would then provide a higher flexibility of the remaining length of the probe which in this case would be particularly suitable for use with a flexible endoscope. As another alternative the entire probe or only portions thereof could be permanently bent with a slight curvature serving the purpose of providing a force opposite to an actuating force which is present with the handling of a flexible endoscope when being controlled on demand to receive a larger radius of movement.

In accordance with a main feature of the present invention the metallic flexible probe is further provided with a predetermined break point at a position indicated by the arrow A in FIG. 1 which is therefore next to the head portion 1 of the probe and approximately at the transition of the head portion to the adjoining initial length 2 of the probe. With the provision of such a predetermined break point care is taken of the possibility that due to a permanent and periodically exposed impact force against the proximal end of the probe by the pneumatically driven projectile of the lithotripter the fatigue of the material could turn up at any arbitrary positon along the length of probe and eventually resulting in a fatigue fracture the position of which would be unknown in advance. The actual object for providing the probe with such a predetermined break point is therefor to encircle such material defaults which might only be developed during the actual use of the probe. The specific position of such a predetermined break point as indicated by the arrow A is therefore chosen under the aspect that at this particular position any fracture of the probe will most presumably not lead to harmful injuries of the patient and to no damages of the surrounding lumen of the endoscope.

Such a predetermined break point could of course be provided by a plurality of different measures. If a thermal treatment of the probe will be envisaged in general for example for the purpose of providing the initial length of the probe with an increased stiffness in comparison with the remaining length of the probe as mentioned above then such a predetermined break point could be predetermined by a thermal treatment as well in such a manner that the probe will receive a lesser strength in the vicinity of the transition between the head portion 1 and the adjoining initial length 2 of the probe.

Alternatively the predetermined break point could also be predetermined by a cross-section of the probe which in the vicinity of this transition is locally limited to a reduced value in comparison with the adjoining initial length of the probe. Such a reduced cross-section would be provided for example by an indentation or a notch of the probe.

Another possibility would be the provision of an adhesive joint between the head portion of the probe and its adjoining initial length. Also a crimp connection between the head portion 1 of the probe and its adjoining initial length 2 could be envisaged as well as a head portion of the probe having a strength which is somewhat less than the strength of the adjoining initial length of the probe and which therefore would be fractured more or less automatically after a predetermined number of hits of the pneumatically driven projectile against the proximal end of the probe.

Whereas a probe having a predetermined break point as predetermined by those different measures as mentioned above could be fastened to the handpiece of a lithotripter by means of a screw cap in the manner as disclosed in U.S. Pat. No. 5,160,336 the present invention actually prefers the more specific fastening of the probe as illustrated in FIG. 2 of the drawing. In the illustrated embodiment the probe is provided with a metallic head 6 which is attached to a proximal end of the probe with a slip-on fit or which is attached to it in any other suitable manner. The metallic head 6 is inserted into an axial bore 7 of a surrounding guide bush 8 which axially guides the proximal end of the probe with an axial extension of the bore 7.

Two flexible O-rings 9 are received in the axial bore 7 and arranged in such a manner as to be slightly prestressed in an axial direction so as to bias the probe which at its proximal end portion is surrounded by these O-rings. The biasing force which is exerted by the two O-rings 9 on the proximal end of the probe therefore acts against the impact force on the exposed face of the metallic head 6 which is caused by the pneumatically driven projectile of the lithotripter. With such an arrangement care is as well taken for averaging the impact energy already at the head portion of the probe and subsequently over the entire length of the probe.

FIG. 2 further illustrates a screw cap 10 holding the guide bush 8 in an axially displaceable manner whereby a further O-ring 11 is provided as a damper acting between the guide bush 8 and the screw cap 10. The guide bush 8 could consist of a flexible material for supplementing the biasing force in particular of the two O-rings 9 whereby especially with such a flexible material of the guide bush 8 it then would also be preferred to prepare the predetermined break point of the probe by an adhesive joint or by a crimp connection between the head portion of the probe and its adjoining initial length. In the illustrated embodiment screw cap 10 actually forms a holding means for removably holding the proximal end of the probe so that by means of this screw cap the probe may be fastenend to the handpiece of a lithotripter in a conventional manner.

We claim:

1. A metallic flexible lithotripsy probe for use as a wave guide for transmission of an impact energy as a shock wave for intracorporeal fragmentation of a calculus, the probe having a nominal diameter that corresponds to a predetermined lumen of an endoscope for use with an intracorporeal lithotripter, the probe comprising:
   a) a head portion at a proximal end of the probe for receiving the impact energy, the head portion having a cross-section which is larger than the probe nominal diameter;
   b) a predetermined break point adapted to break prior to any other points on the probe, the break point located adjacent the head portion approximately at a transition to an adjoining initial length of the probe having the nominal diameter; and
   c) a tip portion at a distal end of the probe.

2. The metallic flexible probe of claim 1, further comprising:
   an intermediate partial length of the probe next to the initial length, the intermediate partial length having a tapered decreasing diameter that tapers to a slightly smaller diameter at an intermediate distal end, an immediately adjoining additional partial length between the intermediate distal end and the tip portion, said tip portion having a tapered increasing diameter that tapers from said slightly smaller diameter to approximately the nominal diameter.

3. The metallic flexible probe of claim 2, wherein the tapered decreasing diameter of the intermediate partial length of the probe comprises a curvature in accordance with a first exponential function.

4. The metallic flexible probe of claim 3, wherein the tapered increasing diameter of the tip portion comprises a curvature according to a second exponential function different than the first exponential function.

5. The metallic flexible probe of claim 2, wherein substantially only a distal face of the tip portion comprises the nominal diameter.

6. The metallic flexible probe of claim 2, wherein the additional partial length is sufficiently small such that the intermediate distal end of the intermediate partial length is essentially immediately adjacent the tapered increasing diameter of the tip portion.

7. The metallic flexible probe of claim 1, wherein the entire probe or portions thereof consist of a nickel-titanium-alloy, a stainless steel, or a combination thereof.

8. The metallic flexible probe of claim 1, wherein at least a first portion of the probe has a first set of material properties that is different than a second set of material properties in a second portion of the probe, the difference between the first and second sets of material properties resulting from:
  (a) the first section comprising a first material that is different than a second material comprising the second portion; or
  (b) the first section comprising a thermally treated section and the second portion comprising an untreated section.

9. The metallic flexible probe of claim 8, wherein the initial length of the probe comprises a thermally treated portion having greater stiffness than a remaining length of the probe.

10. The metallic flexible probe of claim 1, wherein the head portion of the probe further comprises:
  a metallic head at the proximal end of the probe;
  a guide bush having an axial bore adapted to receive said metallic head; and
  at least one slightly axially prestressed seal ring disposed within the guide bush axial bore proximally of the metallic head.

11. The metallic flexible probe of claim 10, wherein the guide bush consists of a flexible material and further comprises a portion of a screw cap adapted for mounting the probe on a handpiece of the intracorporeal lithotripter.

12. The metallic flexible probe of claim 1, wherein the predetermined break point comprises a thermally treated section of the probe that locally weakens the strength of the probe in the vicinity of said transition.

13. The metallic flexible probe according to claim 1, wherein the predetermined break point comprises a locally limited cross-section of the probe that is smaller than a cross-section of the adjoining initial length of the probe.

14. The metallic flexible probe of claim 1, wherein the predetermined break point comprises an indentation or a notch of the probe in the vicinity of said transition.

15. The metallic flexible probe of claim 1, wherein the predetermined break point comprises an adhesive joint between the head portion of the probe and the adjoining initial length.

16. The metallic flexible probe of claim 1, wherein the predetermined break point comprises a crimp connection between the head portion of the probe and the adjoining initial length.

17. The metallic flexible probe of claim 1, further comprising a difference in strength between the head portion, having a first strength, and the adjoining initial length, having a second, somewhat greater strength, wherein the predetermined break point arises from the difference in strength.

18. A flexible lithotripsy probe, having a proximal end and a distal end, the probe adapted for insertion into an endoscope for transmission of impact energy from the proximal end to the distal end to create a shock wave for causing intracorporeal fragmentation of a calculus in contact with the distal end, the probe comprising:
  a head portion at the proximal end;
  an initial portion adjoining the head portion;
  a tip portion at the distal end; and
  a predetermined break point adjacent the head portion approximately at a transition between the head portion and the initial portion, the predetermined break point comprising a section of the probe that is weaker than remaining sections of the probe and that is designed to fracture from repeated exposure to the impact energy prior to any of the remaining sections of the probe fracturing from said repeated exposure.

19. The metallic flexible lithotripsy probe of claim 18 wherein the predetermined break point comprises a feature that weakens the break point relative to the remaining sections of the probe, the feature selected from the group consisting of: a thermally treated section; a reduced cross-section; an indentation; a notch; an adhesive joint; a crimp connection; and an interface between a first material strength in the head portion and a second material strength in the initial portion that is less than the first material strength.

* * * * *